United States Patent [19]

Dorn et al.

[11] 4,029,772

[45] June 14, 1977

[54] PEPTIDE CARBAZATES

[75] Inventors: Conrad P. Dorn, Plainfield; Shu S. Yang, Piscataway, both of N.J.

[73] Assignee: Merck & Co., Inc., Rahway, N.J.

[22] Filed: Dec. 23, 1975

[21] Appl. No.: 643,722

[52] U.S. Cl. .......................... 424/177; 260/112.5 R
[51] Int. Cl.² ...................................... A61K 37/00
[58] Field of Search ............. 260/112.5 R; 424/177

[56] References Cited

UNITED STATES PATENTS

| 3,888,840 | 6/1975 | Failli et al. | 260/112.5 R |
| 3,904,593 | 9/1975 | Immer et al. | 260/112.5 R |

*Primary Examiner*—Delbert R. Phillips
*Attorney, Agent, or Firm*—R. J. Anderson, Jr.; H. E. Westlake, Jr.; F. M. Mahon

[57] ABSTRACT

Certain novel peptide carbazates, their preparation, pharmaceutical compositions and novel methods of treating pancreatitis.

8 Claims, No Drawings

PEPTIDE CARBAZATES

BACKGROUND OF THE INVENTION

This invention relates to a novel class of peptide carbazates useful for selectively inhibiting elastase, a proteolytic enzyme. Certain clinical symptoms found in pancreatitis, emphysema and rheumatoid arthritis are believed to be caused by uncontrolled elastase in the affected tissues.

It is an object of this invention to find a novel group of elastase inhibitors useful for treating pancreatitis. Another object of this invention is to find a novel group of enzyme inhibitors which will selectively react with elastase.

DETAILED DESCRIPTION OF THE INVENTION

We have found that certain peptide carbazates will selectively inhibit elastase by blocking the enzyme. These peptide carbazates may be used to treat pancreatitis. The novel peptide carbazates of this invention have the following structural formula

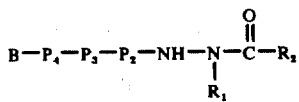

wherein
B is $C_{1-5}$alkanoyl (such as acetyl), t-butoxycarbonyl or carbobenzyloxy,
$P_4$ is alanyl or prolyl,
$P_3$ is alanyl,
$P_2$ is prolyl or leucyl,
$R_1$ is $C_{1-5}$alkyl (such as methyl), and
$R_2$ is $C_{1-5}$alkoxy (such as ethoxy) benzyloxy, or amino-$C_{1-5}$alkoxy (such as 5-aminoamyloxy).

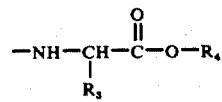

wherein
$R_3$ is $C_{1-5}$alkyl (such as methyl), benzyl and
$R_4$ is $C_{1-5}$alkyl (such as ethyl) or benzyl.
In a preferred embodiment,
B is $C_{1-5}$alkanoyl,
$R_1$ is methyl or isopropyl,
$R_2$ is ethoxy or

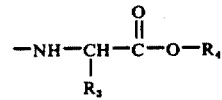

wherein
$R_3$ is methyl or isopropyl, and
$R_4$ is ethyl.
In a more preferred embodiment,
B is acetyl,
$P_2$ is prolyl,
$R_1$ is methyl, and
$R_2$ ethoxy or

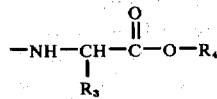

wherein
$R_3$ is methyl, and
$R_4$ is ethyl.

The following novel compounds are representative of the invention:
Acetylalanylalanylprolyl-2-azaalanine ethyl ester,
Acetylprolylalanylprolyl-2-azaalanine ethyl ester,
Acetylalanylalanylprolyl-2-azaalanylalanine ethyl ester,
Acetylalanylalanylprolyl-2-azavaline ethyl ester,
Acetylprolylalanylprolyl-2-azavaline ethyl ester,
Acetylalanylalanylprolyl-2-azavalylalanine ethyl ester,
Acetylalanylalanylprolyl-2-azaalanylvaline ethyl ester, and
Acetylalanylalanylprolyl-2-azavalylvaline ether ester.

Another aspect of this invention relates to the novel pharmaceutical compositions for treating pancreatitis, comprising a non-toxic pharmaceutically acceptable carrier and a compound of formula I, supra, wherein B, $P_4$, $P_3$, $P_2$, $R_1$ and $R_2$ are as defined above.

The non-toxic pharmaceutically acceptable carrier may be, for example, either a solid or a liquid. Exemplary of solid carriers are lactose, corn starch, gelatin, talc, stereotix, stearic acid, magnesium stearate, terra alba, sucrose, agar, pectin, acacia and carboxymethylcellulose (CMC). Exemplary of liquid carriers are peanut oil, olive oil, sesame oil, ethyl alcohol, glycerin and water. Similarly, the carrier or diluent may contain a time delay material, such as glyceryl monostearate or glyceryl distearate, alone or with a wax.

Several pharmaceutical forms of the therapeutically useful compositions may be used. For example, if a solid carrier is used, the compositions may take the form of tablets, capsules, powders, troches or lozenges, prepared by standard pharmaceutical techniques. If a liquid carrier is used the preparation may be in the form of a soft gelatin, syrup, a liquid solution, a liquid emulsion or a liquid suspension. The liquid may be sprayed by aerosol or nebulizer. Suppositories may be prepared in the conventional manner by mixing the compounds of this invention with a suitable non-irritating excipient which is solid at room temperature. Exemplary of excipients are cocoa butter and polyethylene glycol. Gels, lotions and aerosol sprays for topical application may be prepared in conventional manners.

The active compounds are orally, or parenterally administered in the therapeutically effective amount to treat pancreatitis. Advantageously, the active compounds will be administered, alone, or in a pharmaceutical composition in an amount of from about 10.0 mg to 100 mg per kg body weight per day (500 mg to 5.0 g per patient per day) of the active compound preferably from about 15 to 150 mg per kilogram body weight per day. The daily dosage may be given in either single or multiple dosages.

Another aspect of this invention is the method of treating pancreatitis by administering to a patient (animal or human) a compound of formula I, supra, admixed with a non-toxic pharmaceutical carrier such as exemplified above. It should be understood that although preferred dosage ranges are given the dose level for any particular patient depends on the activity of the specific compound employed. Also many other factors that modify the actions of drugs will be taken into account by those skilled in the art in the therapeutic use of medicinal agents, particularly those described above; for example, body weight, sex, diet, time of administration, route of administration, rate of excretion, drug combination, reaction sensitivities and severity of the particular disease.

Another aspect of this invention is the process for preparing the novel compounds of formula I, supra, where B, $P_4$, $P_3$, $P_2$, $R_1$ and $R_2$ are as defined above by reacting a compound of formula II,

with a compound of formula III,

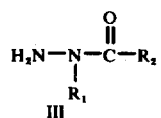

wherein X is hydroxy, halo, p-nitrophenoxy, $-O-P_2-P_3-P_4-B$ or

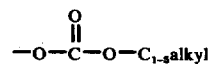

and B, $P_4$, $P_3$, $P_2$, $R_1$ and $R_2$ are defined above. It is preferred to carry the reaction out in an inert solvent. The solvent is not critical. Examples of suitable solvents are ethers (such as tetrahydrofuran (THF)), halogenated hydrocarbons (such as chloroform), and $C_{1-3}$ nitriles (such as acetonitrile). The reaction temperature is generally about −20° to 100° C preferably −20° to +20° C and in the case of mixed anhydrides, −20° to 0° C. The time of reaction is not critical and generally the reaction is carried out until it is essentially complete. The pressure is not critical and generally the reaction is carried out at atmospheric pressure in an open system. When X is halo, the reaction may be carried out in the presence of an acid acceptor (such as pyridine). The product of the reaction, compounds of formula I, may be recovered in the conventional manner, such as by filtration and evaporation of the filtrate to yield the compound of formula I. The compound of formula I may be purified by chromatographing it on a silica gel column using a solvent system such as methanol in chloroform.

The following examples are given to illustrate the invention and are not intended to limit it in any manner. All parts are given in parts by weight unless otherwise expressed. All temperatures are given in degrees centigrade (° C) unless otherwise expressed.

EXAMPLE 1

Acetylalanylalanylprolyl-2-azaalanine ethyl ester

Step A — Preparation of 2-azaalanine ethyl ester

To a stirred solution of methylhydrazine (10 mmole) and triethylamine (10 mmole) in dry tetrahydrofuran (20 ml) at 0° to 5° C is added a solution of ethyl chloroformate (7 mmole) in tetrahydrofuran (10 ml) dropwise. After the addition, the reaction mixture is allowed to warm to room temperature over a period of 1 hour and stirred for a further 2 hours. The precipitate (triethylamine hydrochloride) is filtered of and the filtrate is evaporated to dryness. Chromatography on silica gel (25 gm) and elution with 1% methanol in chloroform gives 2-azaalanine ethyl ester.

Step B — Preparation of acetylalanylalanylprolyl-2-azaalanine ether ester

To a stirred solution of acetylalanylalanylproline (2 mmole) and N-methylmorpholine (2 mmole) in dry tetrahydrofuran (20 ml) at −20° to −25° C is added isobutyl chloroformate (2 mmole). After 5 minutes a solution of 2-azaalanine ethyl ester (2 mmole) in tetrahydrofuran (3 ml) is added dropwise and the reaction mixture is allowed to warm to room temperature over a period of 1 hour and stirred for a further 4 hours. The precipitate is filtered off and the filtrate is evaporated to dryness. Chromatograhy on silica gel (50 gm) and elution with 10% methanol in chloroform gives pure acetylalanylalanylprolyl-2-azaalanine ethyl ester.

EXAMPLE 2

Acetylprolylalanylprolyl-2-azaalanine ethyl ester

To a stirred solution of acetylprolylalanylprolyline (2 mmole) and N-methylmorpholine (2 mmole) in dry tetrahydrofuran (600 ml) at −20° to −25° C is added isobutyl chloroformate (2 mmoles). After 10 minutes a solution of 2-azaalanine ethyl ester (2 mmole, Example 1A, Step A) in tetrahydrofuran (3 ml) is added dropwise and the reaction mixture is allowed to warm to room temperature over a period of 1 hour and stirred overnight. The precipitate is filtered off and the filtrate is concentrated to dryness. Chromatography on silica gel (45 gm) and elution with 10% methanol in chloroform affords acetylprolylalanylprolyl-2-azaalanine ethyl ester.

EXAMPLE 3

Acetylalanylalanylprolyl-2-azaalanylalanine ethyl ester

Step A — Preparation of 2-azaalanylalanine ethyl ester

To a stirred solution of methylhydrazine (0.07 mole) and triethylamine (0.06 mole) in dry tetrahydrofuran (100 ml) at 0° to 5° C is added (1-ethoxycarbonyl)-ethylisocyanate (0.06 mole) over a period of 1 hour. The reaction mixture is allowed to warm to room temperature for 1 hour and filtered. The filtrate is evaporated to dryness and the residue is recrystallized from ether to give pure 2-azaalanylalanine ethyl ester, m.p. 77°–79.5° C.

Step B — Acetylalanylalanylprolyl-2-azaalanylanine ethyl ester

To a solution of acetylalanylalanylproline (3 mmole) and N-methylmorpholine (3 mmole) in dry tetrahydrofuran (110 ml) at −20° to −25° C is added isobutyl chloroformate (3 mmole) and stirred at −20° C for 10 minutes. A solution of 2-azaalanylalanine ethyl ester (3 mmole) in tetrahydrofuran (15 ml) is added dropwise. The resulting mixture is allowed to warm to room temperature over a period of 1 hour and stirred overnight. The precipitate is filtered off and the filtrate is concentrated to dryness. Chromatography on silica gel (70 gm) and elution with 8% methanol in chloroform gives acetylalanylalanylprolyl-2-azaalanylalanine ethyl ester.

EXAMPLE 4

Carbobenzyloxyalanylalanylprolyl-2-azaalanine ethyl ester

Step A — t-Butoxycarbonylalanylprolyl-2-azaalanine ethyl ester

To 0.16 mole of t-butoxycarbonylalanylproline in 80 ml of dry tetrahydrofuran which has been cooled to −20° to −30° is added 2 ml of N-methylmorpholine and then 2.1 ml of isobutylchloroformate. After stirring for 10 minutes, 0.16 mole of 2-azaalanine ethyl ester and 60 ml of chloroform are added. The reaction mixture is allowed to warm to room temperature overnight, concentrated in vacuo, taken up in ethyl acetate and the insoluble material removed by filtration. Concentration of the filtrate in vacuo gives t-butoxycarbonylalanylprolyl-2-azaalanine ethyl ester.

Step B — Alanylprolyl-2-azaalanine ethyl ester.

To the t-butoxycarbonylalanylprolyl-2-azaalanine ethyl ester obtained above is added 15 ml of methylene chloride. The reaction mixture is cooled to 0° and 15 ml of trifluoroacetic acid added. After stirring for 1 hour at 0° and 1 hour at room temperature, the reaction mixture is concentrated in vacuo to yield alanylprolyl-2-azaalanine ethyl ester as its trifluoroacetic acid salt.

Step C — Carbobenzyloxyalanylalanylprolyl-2-azaalanine ethyl ester

To a solution of 0.005 mole of carbobenzyloxyalanine in 100 ml of dry tetrahydrofuran which has been cooled to −20° to −30° is added 1 ml of N-methylmorpholine and then 1 ml of isobutyl-chloroformate. After stirring for 10 minutes there is added 0.005 mole of alanylprolyl-2-azaalanine ethyl ester trifluoroacetic acid salt, 60 ml of chloroform and 1 ml of N-methylmorpholine. The reaction mixture is stirred overnight at room temperature, concentrated in vacuo, the residue treated with ethylacetate and the insoluble material removed by filtration. The filtrate is concentrated in vacuo and the residue chromatographed on a silica gel. Elution with ethyl acetate gives carbobenzyloxyalanylalanylprolyl-2-azaalanine ethyl ester.

EXAMPLE 5 t-Butyloxycarbonylalanylalanylprolyl-2-azaalanine ethyl ester

Step A — t-Butyloxycarbonylalanylalanylproline benzyl ester

To a solution of 0.035 mole of t-butyloxycarbonylalanine in 80 ml of dry tetrahydrofuran which has been cooled to −20° to −30° is added 4 ml of N-methylmorpholine and then 4.6 ml of isobutylchloroformate. After stirring for 10 minutes there is added 0.035 mole of alanylproline benzylester hydrochloride and 4 ml of N-methylmorpholine in 60 ml of chloroform. The reaction mixture is stirred overnight at room temperature, concentrated in vacuo and the residue taken up between ethyl acetate and 0.25 N hydrochloric acid. The organic layer is separated, washed with saturated sodium bicarbonate, water, dried over magnesium sulfate and concentrated in vacuo to give t-butoxycarbonylalanylalanylproline benzyl ester.

Step B — t-Butyloxycarbonylalanylalanylproline

A solution of 0.015 moles of t-butyloxycarbonylalanylalanylproline benzyl ester in 50 ml of methanol is reduced with hydrogen at 40 lbs pressure in the presence of 1 gm of 10% Pd/C. The reaction mixture is filtered and concentrated in vacuo to give t-butyloxycarbonylalanylalanylproline.

Step C — t-Butyloxycabonylalanylalanylprolyl-2-azaalanine ethyl ester

To a solution of 0.009 moles of t-butyloxycarbonylalanylalanylproline in 80 ml of dry tetrahydrofuran which has been cooled to −20° to −30° is added 1.0 ml of N-methylmorpholine and 1.2 ml of isobutylchloroformate. After stirring for 10 minutes there is added 0.009 moles of 2-azaalanine ethyl ester in 50 ml of chloroform. The reaction mixture is stirred overnight at room temperature and then concentrated in vacuo. The residue is taken up between ethyl acetate and 0.25 N hydrochloric acid. The organic layer is separated, washed with saturated sodium bicarbonate solution, water, dried over magnesium sulfate and concentrated in vacuo. The residue is chromatographed on silica gel. Elution with ethyl acetate gives t-butyloxycarbonylalanylalanylprolyl-2-azaalanine ethyl ester.

EXAMPLE 6

PARENTERAL FORMULATIONS

Step A — Preconstituted Solutions

| | |
|---|---|
| AAEE* | 50 mg |
| Sodium chloride | 9.0 mg |
| NaOH or HCl | q.s. to pH 5–6 |
| Water for Injection | q.s. 1.0 ml |

*AAEE is an abbreviation used for acetylalanylalanylprolyl-2-azaalanine-dl ethyl ester.

Other concentrations of preconstituted solutions of AAEE cover the range of 50-250 mg/ml as required for therapy. Suitable buffering agents such as citric acid, sodium phosphate, TRIS, and the like may be added to the above compositions. Additionally, other pharmaceutical adjuvants such as antioxidants, chelating agents commonly employed in the formulation of parenteral formulations may be added to enhance the stability and pharmaceutical elegance of the compositions noted above. Compositions may also contain benzylalcohol (9 mg per ml) or methylparaben and propylparaben (1.5 mg/ml and 0.2 mg/ml).

Preconstituted solutions of AAEE are prepared by dissolving the ingredients in water for injection, adjusting the pH of the solutions to 5-6 and diluting to volume. The solutions are rendered sterile by absolute filtration and aseptically subdivided into sterile containers.

Step B — Cryodessicated AAEE

| | |
|---|---|
| AAEE | 50 mg |
| Mannitol | 50 mg |
| NaOH or HCl | q.s. to pH 5–6 |
| Water for Injection | q.s. 1.0 ml. |

Compositions noted above may contain phenylmercuric acetate 0.1% as a preservative. Cryodessicated AAEE formulations are prepared by dissolving the ingredients and rendering the solution sterile by absolute filtration. Aliquots of the sterile solution are aseptically transferred to sterile vials. The vials are transferred to a freeze dryer and processed in the usual fashion. Other cryodessicated potencies of AAEE range from 50 to 250 mg per vial as required for therapy.

Similarly, an equivalent amount of acetylprolylalanylprolyl-2-azaalanine ethyl ester or acetylalanylalanylprolyl-2-azaalanylalanine ethyl ester may be substituted for the acetylalanylalanylprolyl-2-azaalanine ethyl ester (AAEE) in the above pharmaceutical compositions.

What is claimed is:

1. A compound of the formula:

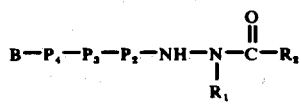

wherein
B is $C_{1-5}$alkanoyl, t-butoxycarbonyl or carbobenzyloxy,
$P_4$ is alanyl or prolyl,
$P_3$ is alanyl,
$P_2$ is prolyl or leucyl
$R_1$ is $C_{1-5}$alkyl,
$R_2$ is $C_{1-5}$alkoxy, benzyloxy or amino $C_{1-5}$alkoxy

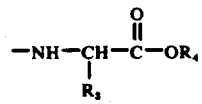

wherein
$R_3$ is $C_{1-5}$alkyl or benzyl, and
$R_4$ is $C_{1-5}$alkyl, or benzyl.

2. The compound of claim 1 wherein
B is $C_{1-5}$alkanoyl,
$R_1$ is methyl or isopropyl, and
$R_2$ is ethoxy or

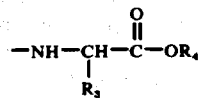

wherein
$R_3$ is methyl or isopropyl, and
$R_4$ is ethyl.

3. The compound of claim 2 wherein
B is acetyl, and
$P_2$ is prolyl,
$R_1$ is methyl and
$R_2$ is ethoxy or

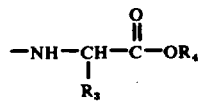

wherein
$R_3$ is methyl, and
$R_4$ is ethyl.

4. The compound of claim 3 wherein $P_4$ is prolyl.

5. The compound of claim 3 wherein $P_4$ is alanyl.

6. Acetylalanylalanylprolyl-2-azaalanine ethyl ester according to claim 5.

7. A pharmaceutical composition comprising a nontoxic pharmaceutically acceptable carrier and a therapeutically effective amount of a compound of the formula:

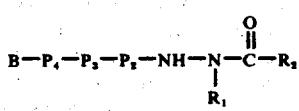

wherein
B is $C_{1-5}$alkanoyl, t-butoxycarbonyl or carbobenzyloxy,
$P_4$ is alanyl or prolyl,
$P_3$ is alanyl,
$P_2$ is prolyl or leucyl,
$R_1$ is $C_{1-5}$alkyl,
$R_2$ is $C_{1-5}$alkoxy, benzyloxy or amino $C_{1-5}$alkoxy,

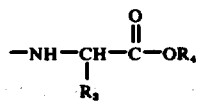

wherein
$R_3$ is $C_{1-5}$alkyl or benzyl, and
$R_4$ is $C_{1-5}$alkyl, or benzyl.

8. A method of treating pancreatitis, which comprises administering to a patient a therapeutically effective amount of a compound of the formula:

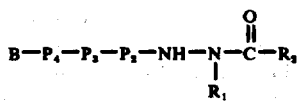

wherein
B is $C_{1-5}$alkanoyl, t-butoxycarbonyl or carbobenzyloxy,
$P_4$ is alanyl or prolyl,
$P_3$ is alanyl,
$P_2$ is prolyl or leucyl,
$R_1$ is $C_{1-5}$alkyl,
$R_2$ is $C_{1-5}$alkoxy, benzyloxy or amino $C_{1-5}$alkoxy

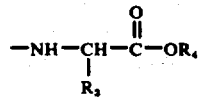

wherein
$R_3$ is $C_{1-5}$alkyl or benzyl, and
$R_4$ is $C_{1-5}$alkyl, or benzyl.

* * * * *